United States Patent
Bauer et al.

(10) Patent No.: US 7,950,864 B2
(45) Date of Patent: *May 31, 2011

(54) DEVICE WITH INTERNAL PULL TAB ACTIVATION

(75) Inventors: Walter G. Bauer, Neenah, WI (US); Marci E. Sojka, Neenah, WI (US); Sarah L. Christoffel, Appleton, WI (US); Cecelia Mary Berger Sharp, Atlanta, GA (US); Michael S. Brunner, Roswell, GA (US); Michael Amante, St. Paul, MN (US); Ann Marie Przepasniak, Sturtevant, WI (US)

(73) Assignee: Kimberly-Clark Worldwide, Inc., Neenah, WI (US)

( * ) Notice: Subject to any disclaimer, the term of this patent is extended or adjusted under 35 U.S.C. 154(b) by 1325 days.

This patent is subject to a terminal disclaimer.

(21) Appl. No.: 11/303,061

(22) Filed: Dec. 13, 2005

(65) Prior Publication Data
US 2007/0134048 A1 Jun. 14, 2007

(51) Int. Cl.
*B43K 5/14* (2006.01)
(52) U.S. Cl. ....................................... 401/132
(58) Field of Classification Search .......... 401/132–135; 605/3
See application file for complete search history.

(56) References Cited

U.S. PATENT DOCUMENTS

| | | | |
|---|---|---|---|
| 3,053,385 A | * | 9/1962 | Spees ........................... 206/361 |
| 3,085,681 A | | 4/1963 | Fazzari |
| 3,565,738 A | | 2/1971 | Kirkpatrick |
| 3,722,174 A | | 3/1973 | Bergevin et al. |
| 3,783,089 A | | 1/1974 | Hurst et al. |
| 3,924,008 A | | 12/1975 | Ford et al. |
| 3,940,905 A | | 3/1976 | Perry, III |
| 3,958,750 A | | 5/1976 | Prybeck |
| 4,190,154 A | | 2/1980 | Clark |
| 4,337,862 A | | 7/1982 | Suter |
| 4,348,440 A | | 9/1982 | Kriozere |
| 4,545,180 A | | 10/1985 | Chung et al. |
| 4,603,069 A | | 7/1986 | Haq et al. |
| 4,638,913 A | | 1/1987 | Howe, Jr. |
| 4,657,802 A | | 4/1987 | Morman |

(Continued)

FOREIGN PATENT DOCUMENTS
DE      1 264 317 B      3/1968
(Continued)

OTHER PUBLICATIONS

Miller, Edward E., "A Simple Test for Dispersion of Wet Chop Fiberglass in Water," *TAPPI Proceedings—1996 Nonwovens Conference*, pp. 71-85.

*Primary Examiner* — Huyen Le
(74) *Attorney, Agent, or Firm* — Denise L. Stoker

(57) ABSTRACT

A stretchable device is provided including a base layer; a wipe layer attached to the base layer at a seam and defining an interior space between the wipe and base layers, the interior space having an internal surface; and a pouch positioned within the interior space and attached to one of the seam and the internal surface, the pouch having a top layer, a bottom layer attached to the top layer to form a cavity therebetween, an opening in one of the top and bottom layers, and a pull tab coupled to the pouch and to one of the seam and the internal surface.

23 Claims, 5 Drawing Sheets

U.S. PATENT DOCUMENTS

| | | | |
|---|---|---|---|
| 4,700,531 A | 10/1987 | Hsu et al. | |
| 4,705,197 A | 11/1987 | Gordon et al. | |
| 4,805,767 A | 2/1989 | Newman | |
| 4,830,187 A | 5/1989 | Keyes et al. | |
| 4,840,270 A | 6/1989 | Caputo et al. | |
| 4,878,775 A | 11/1989 | Norbury et al. | |
| 4,889,234 A | 12/1989 | Sorensen et al. | |
| 4,890,744 A | 1/1990 | Lane, Jr. et al. | |
| 4,902,142 A | 2/1990 | Lammert et al. | |
| 4,910,292 A | 3/1990 | Blount | |
| 4,973,656 A | 11/1990 | Blount | |
| 4,978,232 A | 12/1990 | Dunton | |
| 5,012,930 A | 5/1991 | Hansen | |
| 5,022,526 A | 6/1991 | Crum | |
| 5,044,776 A | 9/1991 | Schramer et al. | |
| 5,059,035 A | 10/1991 | Kristensen | |
| 5,060,847 A | 10/1991 | Angus | |
| 5,090,832 A | 2/1992 | Rivera et al. | |
| 5,111,932 A | 5/1992 | Campbell | |
| 5,140,796 A | 8/1992 | Pope | |
| RE34,117 E | 10/1992 | Martin et al. | |
| 5,154,293 A | 10/1992 | Gould | |
| 5,161,687 A | 11/1992 | Kornell et al. | |
| 5,167,674 A | 12/1992 | Ika | |
| 5,169,251 A | 12/1992 | Davis | |
| 5,221,143 A | 6/1993 | Peppiatt | |
| 5,273,514 A | 12/1993 | Kristensen | |
| 5,312,883 A | 5/1994 | Komatsu et al. | |
| 5,317,063 A | 5/1994 | Komatsu et al. | |
| 5,348,400 A | 9/1994 | Haiss et al. | |
| 5,382,400 A | 1/1995 | Pike et al. | |
| 5,417,040 A | 5/1995 | Davoren | |
| 5,443,154 A | 8/1995 | Hustad et al. | |
| 5,509,913 A | 4/1996 | Yeo | |
| 5,514,442 A | 5/1996 | Galda et al. | |
| 5,604,000 A | 2/1997 | May | |
| 5,616,201 A | 4/1997 | Finch et al. | |
| 5,674,010 A | 10/1997 | Dussich | |
| 5,695,868 A | 12/1997 | McCormack | |
| 5,725,311 A | 3/1998 | Ponsi et al. | |
| 5,733,636 A | 3/1998 | May | |
| 5,770,528 A | 6/1998 | Mumick et al. | |
| 5,823,685 A | 10/1998 | Garlichs | |
| 5,824,380 A | 10/1998 | Hagen | |
| 5,843,056 A | 12/1998 | Good et al. | |
| 5,855,434 A | 1/1999 | Hagen | |
| 5,916,678 A | 6/1999 | Jackson et al. | |
| 5,937,615 A | 8/1999 | Forman | |
| 5,944,425 A | 8/1999 | Forman | |
| 5,948,710 A | 9/1999 | Pomplun et al. | |
| 5,952,251 A | 9/1999 | Jackson et al. | |
| 5,956,770 A | 9/1999 | Dennis | |
| 5,956,794 A | 9/1999 | Skiba et al. | |
| 5,971,971 A | 10/1999 | Saint-Ramon et al. | |
| 6,032,854 A | 3/2000 | Greer et al. | |
| 6,048,100 A | 4/2000 | Thrall et al. | |
| 6,113,271 A | 9/2000 | Scott et al. | |
| 6,126,009 A | 10/2000 | Shiffler et al. | |
| 6,171,292 B1 | 1/2001 | Osborn, III et al. | |
| 6,315,448 B1 | 11/2001 | Thrall | |
| 6,341,602 B1 | 1/2002 | Fulcher | |
| 6,350,057 B1 | 2/2002 | Forman | |
| 6,420,006 B1 | 7/2002 | Scott | |
| 6,428,867 B1 | 8/2002 | Scott et al. | |
| 6,508,602 B1 | 1/2003 | Gruenbacher et al. | |
| 6,588,961 B2 | 7/2003 | Lafosse-Marin et al. | |
| 6,589,622 B1 | 7/2003 | Scott | |
| 6,669,387 B2 * | 12/2003 | Gruenbacher et al. | 401/7 |
| 6,755,927 B2 | 6/2004 | Forman | |
| 2001/0010253 A1 | 8/2001 | Forman | |
| 2003/0039412 A1 | 2/2003 | Rodick | |
| 2003/0094466 A1 | 5/2003 | Duquet et al. | |
| 2004/0101214 A1 | 5/2004 | Feder | |
| 2004/0237235 A1 | 12/2004 | Visioli et al. | |
| 2005/0148959 A1 | 7/2005 | Przepasniak et al. | |
| 2005/0201812 A1 | 9/2005 | Wong et al. | |
| 2005/0244211 A1 | 11/2005 | Brunner et al. | |
| 2006/0251464 A1 | 11/2006 | Bauer et al. | |
| 2007/0048063 A1 | 3/2007 | Bauer et al. | |

FOREIGN PATENT DOCUMENTS

| | | |
|---|---|---|
| DE | 93 16 908 U1 | 4/1994 |
| DE | 298 01 621 U1 | 4/1998 |
| EP | 0 074 161 A2 | 3/1983 |
| EP | 0 175 451 A2 | 3/1986 |
| EP | 0 258 143 A1 | 3/1988 |
| EP | 0 279 632 A2 | 8/1988 |
| EP | 0 442 292 A1 | 8/1991 |
| EP | 0 453 105 A2 | 10/1991 |
| EP | 0 276 554 B1 | 3/1992 |
| EP | 0 517 566 B1 | 3/1995 |
| EP | 0 367 744 B1 | 6/1995 |
| EP | 0 658 480 A1 | 6/1995 |
| EP | 0 675 703 A1 | 10/1995 |
| EP | 0 829 433 A2 | 3/1998 |
| EP | 0 841 049 A1 | 5/1998 |
| EP | 0 990 511 A2 | 4/2000 |
| EP | 1 046 591 A2 | 10/2000 |
| EP | 1 198 512 A1 | 4/2002 |
| EP | 0 968 928 B1 | 3/2003 |
| EP | 1 375 380 A1 | 1/2004 |
| EP | 1 480 895 A1 | 12/2004 |
| EP | 1 217 914 B1 | 4/2005 |
| JP | 09-127874 A | 5/1997 |
| JP | 10-129745 A | 5/1998 |
| JP | 11-292164 A | 10/1999 |
| JP | 2000-168801 A | 6/2000 |
| JP | 2001-301807 A | 10/2001 |
| JP | 2004-189319 A | 7/2004 |
| NL | 1 021 437 C1 | 11/2003 |
| WO | WO 79/00590 A1 | 8/1979 |
| WO | WO 93/08982 A2 | 5/1993 |
| WO | WO 95/28331 A1 | 10/1995 |
| WO | WO 99/05045 A1 | 2/1999 |
| WO | WO 99/46182 A2 | 9/1999 |
| WO | WO 01/26499 A1 | 4/2001 |
| WO | WO 02/30251 A2 | 4/2002 |
| WO | WO 03/000106 A1 | 1/2003 |
| WO | WO 03/059776 A1 | 7/2003 |
| WO | WO 2006/121598 A1 | 11/2006 |
| WO | WO 2007/027277 A1 | 3/2007 |

* cited by examiner

US 7,950,864 B2

DEVICE WITH INTERNAL PULL TAB ACTIVATION

BACKGROUND

This invention pertains to cleaning, absorbent, and application devices, and containers for liquids.

Cleaning devices and other similar devices that include a fluid container commonly include a bladder or liquid-containing pouch. Such pouches are designed to burst along a frangible seam or portion when pressure is applied to the device and therefore the pouch. Such devices are not selective and burst under sufficient pressure, whether that pressure is applied intentionally by a user, or that pressure is applied unintentionally during handling, shipping, or storage.

SUMMARY

Cleaning devices and other similar devices including bladders that contain fluids suffer from the problem of premature bursting of such liquid containing pouches. In addition, some cleaning devices and other similar devices including pouches that contain fluids also include an external or removable pull tab that must be disposed of after the device is activated. In addition, some cleaning devices have one of a water-tight container, where the container is easy to open, but not both, leading to shelf integrity issues.

The invention disclosed herein solves the premature bursting problem by providing a device including a soft flexible pouch of fluid and a pull tab. The flexible pouch is durable and is designed to not burst during normal handling. The device balances shelf integrity (to prevent premature bursting) and ease of use. The device includes a water-tight container that opens easily, and is relatively inexpensive to manufacture.

More specifically, the present invention provides a device including a base layer; a wipe layer attached to the base layer at a seam and defining an interior space between the wipe and base layers, the interior space having an internal surface; and a pouch positioned within the interior space and attached to one of the seam and the internal surface, the pouch having a top layer, a bottom layer attached to the top layer to form a cavity therebetween, an opening in one of the top and bottom layers, and a pull tab coupled to the pouch and to one of the seam and the internal surface.

The present invention also provides a device including a base layer; a wipe layer attached to the base layer to form an internal space therebetween; a means for containing a fluid positioned within the internal space, and a means for unsealing the fluid-containing means, wherein the unsealing means is activated by stretching one of the wipe and base layers.

The present invention also provides a method for using a device, the method including producing a device including a base layer and a wipe layer attached to the base layer at a seam and defining an interior space between the wipe and base layers, the interior space having an internal surface, wherein one of the wipe and base layers is stretchable; and activating the device by stretching the device.

The present invention also provides a method for using a device, the method including producing a device including a base layer; a wipe layer attached to the base layer at a seam and defining an interior space between the wipe and base layers, the interior space having an internal surface; and a pouch positioned within the interior space and attached to one of the seam and the internal surface, the pouch having a top layer, a bottom layer attached to the top layer to form a cavity therebetween, an opening in one of the top and bottom layers, and a pull tab coupled to the pouch and to one of the seam and the internal surface. The method also includes activating the device by stretching the device to open the opening.

The present invention also provides a device including a base layer; a wipe layer attached to the base layer at a seam and defining an interior space between the wipe and base layers, the interior space having an internal surface, wherein at least one of the wipe and base layers is stretchable; and a pouch positioned within the interior space and attached to one of the seam and the internal surface, the pouch having a top layer, a bottom layer attached to the top layer to form a cavity therebetween, an opening in one of the top and bottom layers, and a pull tab coupled to the pouch and to one of the seam and the internal surface.

The present invention also provides a device including a stretchable wipe layer formed to define an interior space, the interior space having an internal surface; and a pouch positioned within the interior space and attached to the internal surface, the pouch having an outer surface, an opening in the outer surface, and a pull tab coupled to the pouch.

Objects and advantages of the present invention will become apparent to those skilled in the art in view of the following description and the accompanying drawings.

DETAILED DESCRIPTION OF THE PREFERRED EMBODIMENTS

The aspects of the invention as described herein will be described for exemplary purposes as a cleaning device. The aspects of the invention, however, apply equally to other forms of products, including absorbent devices, application devices, personal care devices, cosmetic devices, and other devices including wipes, mops, mitts, and cleaning towels, among other devices, and to all suitable uses including cleaning, applying, and removing.

The term "surface" and its plural generally refer herein to the outer or the topmost boundary of an object. Surface may refer to that of skin, hair, clothing, upholstery, countertops, floors, walls, windows, tables, appliances, bathroom fixtures, automobiles, or any other object that may require or accommodate cleaning, removing something from, or applying something to its surface.

The term "stretchable" generally refers to the capability of a material to be either elastically or plastically extensible. An elastically extensible or elastically stretchable material is a material that is capable of extending upon application of a tensile force and capable of retracting either partially or close to completely to its original dimension(s) upon removal of the force. A plastically extensible material is a material that is capable of extension or deformation without breaking upon application of a tensile force, but does not substantially recover its original size and shape after removal of a force causing the extension or deformation.

Described herein is a disposable cleaning device 10 for the removal of dirt, etc. from a surface. Such a cleaning device 10 allows a user to clean a surface.

Figure 1:
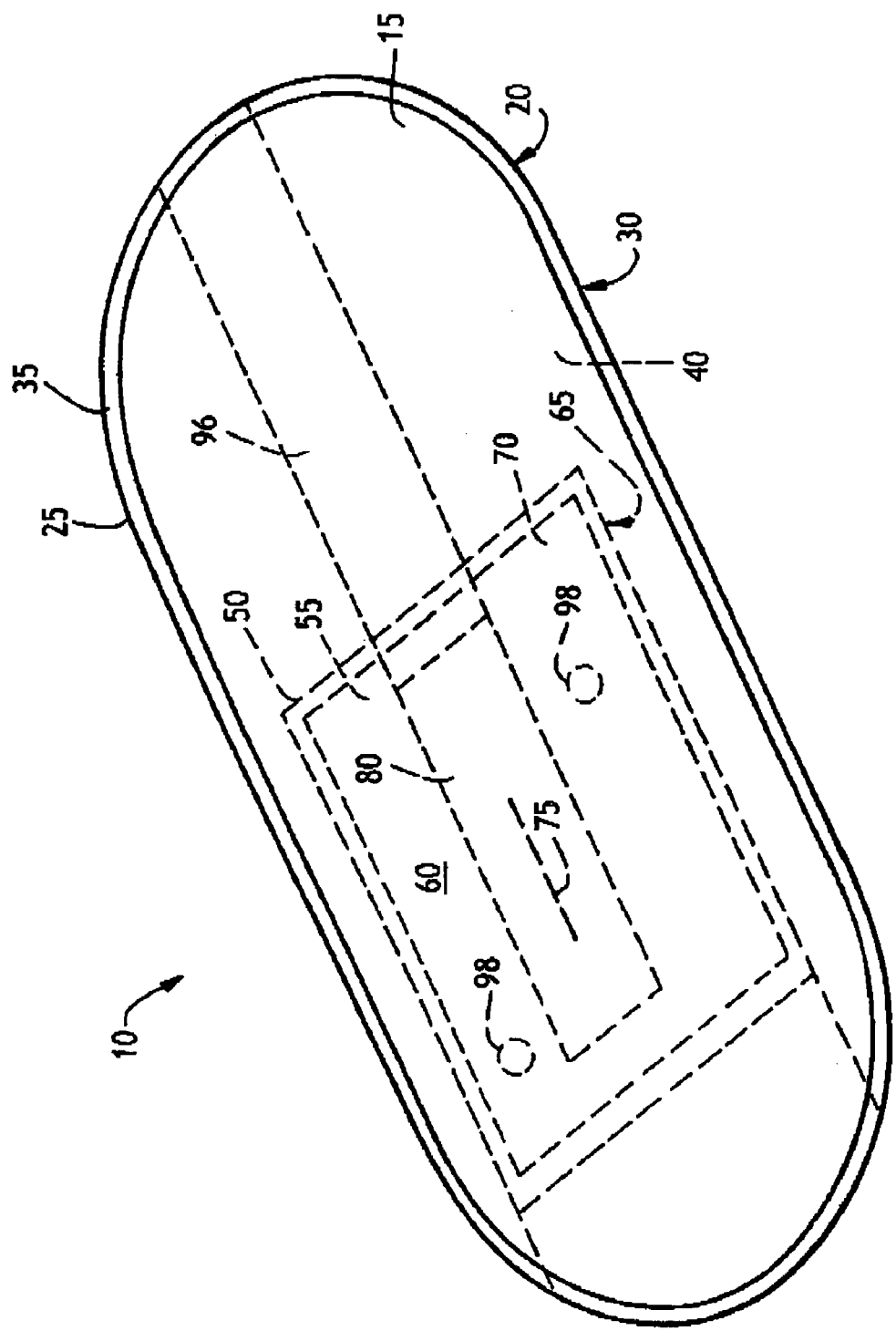
FIG. 1 is a schematic perspective view of an aspect of the present invention.

FIG. 1 illustrates an example of a cleaning device 10 as an aspect of the present invention. The device 10 includes a wipe layer 15 and a base layer 20. For purposes of illustration, and not for purposes of limitation, the cleaning device 10 is described as a pad.

The device 10 includes a wipe layer 15. The wipe layer 15 may be of any suitable shape, but is preferably generally planar and is further preferably generally rectangular or oblong. The wipe layer 15 has a perimetric edge 25 extending around the wipe layer 15. In one aspect of the present invention, the wipe layer 15 is generally the size of a human hand held flat on a surface. In another aspect of the present invention, the wipe layer 15 is generally the size of the four fingers of a human hand. In still another aspect of the present invention, the wipe layer 15 is generally the size of a human finger. The device 10 may be manufactured in any shape or of any dimensions, including as a pad sized to fit best in a child's hand, an adult hand, or on any cleaning implement. In general, the wipe layer 15 may be of any suitable size, with the size preferably selected to be suitable for the intended use of the cleaning device 10. In other aspects of the present invention, the device 10 can be manufactured into other shapes such as a mitt or square or round pads, etc.

The wipe layer 15 is an active layer, which performs the cleaning function. The wipe layer 15 is stretchable, and may be either elastically or plastically stretchable. In alternate aspects of the present invention, any suitable coform, nonwoven, or woven material may be used. In one aspect of the present invention, the wipe layer 15 is an absorbent material. The wipe layer 15 may be a stretch-bonded laminate (SBL) with pre-stretched elastic filament and meltblown material with one ply of spunbond material on each outer surface and a basis weight of approximately 70 gsm, but any suitable absorbent material may be used. SBL and other composite nonwoven elastic webs are further described in U.S. Pat. No. 4,657,802 to Morman. In one aspect of the present invention, the wipe layer 15 includes a dry embossed 110 grams per square meter (gsm) coform laminate available from Kimberly-Clark Corporation.

In other aspects of the present invention, materials for the wipe layer 15 may include cotton, rayon, wood pulp, and polymeric substances such as nonwoven fabrics, foam sponges, and thermoplastics. The material may be formed of a nonwoven fabric that is made of interbonded thermoplastic fibers. The fibers may be formed from a variety of thermoplastic materials including polyolefins (e.g., polyethylene or polypropylene), polystyrene, and polyamides (e.g., nylon). In addition, thermoplastic polymers that are elastomeric may also be used as fibers, including polyurethanes and block copolymers. Blends of any of these materials may be used to form the fibers. The fibers may include additives (e.g., wax, pigments, stabilizers, and fillers) that are inserted as the fibers are fabricated to achieve one or more desired properties within the fibers. Some example additives include compatible surfactants that are added to the polymers to make the surface of the fibers more wettable, thereby improving the ability of the fiber structure to attract unwanted debris away from the skin. The amount of surfactant added to the fibers can be adjusted to control the surface wetting of the fabric formed from the fibers. Examples of suitable surfactants include sodium dioctyl sulfosuccinate and alkyl phenoxy ethanol.

Material used in making the wipe layer 15 may be capable of capturing and/or storing substances within the material. Such material may store and/or capture debris, cleansers, lubricants, spermicidal agents, and medications, among other materials, before or while using the device 10. Examples of such materials include spunbond, spunlace, bonded carded web, and apertured film materials. In one aspect of the present invention, the material is an apertured film that is formed of a polyolefin that may be combined with a nonwoven fabric. In other aspects of the present invention, the material of the wipe layer 15 may be a laminate of like, similar, or different tissue, nonwoven, woven, or film materials, or of any other materials described herein. With some materials such as spunlace, pulling on the ends of the device 10 may cause the device 10 to reduce in width at the middle of the device 10. Should this happen, a user may restore the shape of the device 10 by lightly pulling on the sides of the device 10.

When a nonwoven fabric is used, the basis weight of the nonwoven fabric may vary depending on the properties that are desired within the device 10. As an example, the basis weight for the nonwoven fabric may be as low as 10 gsm and as high as 300 gsm. Such nonwoven materials may include a textured surface. Examples of such nonwoven textured materials include rush transfer materials, flocked materials, wireform nonwovens, and thermal point unbonded materials, among others.

In one aspect of the present invention, the wipe layer 15 may be used dry to absorb liquids from a surface. In another aspect of the present invention, the wipe layer 15 may be dampened by a user with water or another substance to aid cleaning with the cleaning device 10.

The cleaning device 10 also includes a base layer 20. The base layer 20 is preferably of the same general size and shape of the wipe layer 15, although the size and/or shape of the base layer 20 may be selected to be different from the size and/or shape of the wipe layer 15 based on the intended use of the cleaning device 10. The base layer 20 has a perimetric edge 30 extending around the perimeter of the base layer 20.

The base layer 20 may be a backing layer. The base layer 20 may be stretchable, and may be either elastically or plastically stretchable. The base layer 20 may be manufactured from any suitable nonwoven, woven, or paper tissue material. In one aspect of the present invention, the base layer 20 is an absorbent material. The base layer 20 may be SBL with pre-stretched filament and meltblown material with one ply of spunbond material on each outer surface and a basis weight of approximately 70 gsm, but any suitable absorbent material may be used. In one aspect of the present invention, the base layer 20 includes a dry embossed 100 gsm coform laminate available from Kimberly-Clark Corporation.

In an alternative aspect of the present invention, the base layer 20 is also an active layer and manufactured under any of the aspects of the present invention described above for the wipe layer 15. In the case of the base layer 20 as an active layer, the base layer 20 may be manufactured from a material similar to or different from that used for the wipe layer 15.

In an alternative aspect of the present invention, one or both of the wipe and base layers 15, 20 may be breathable to allow air to circulate through the device 10.

The wipe layer 15 is coupled to the base layer 20. One of the wipe and base layers 15, 20 is positioned to overlie the other of the wipe and base layers 15, 20, such that the perimetric edges 25, 30 of the wipe and base layers 15, 20 generally align. A portion of the perimetric edge 25 of the wipe layer 15 is attached to the perimetric edge 30 of the base layer 20 to form a seam 35 and an interior space 40. The seam 35 may be formed at the perimetric edges 25, 30, or the seam 35 may be adjacent or inward from the perimetric edges 25, 30. The wipe and base layers 15, 20 may be attached by adhesive, ultrasonic bonding, heating, sewing, or by any other suitable method. In one aspect of the present invention, the wipe and base layers 15, 20 are attached using a block copolymer adhesive such as 34-5610 construction adhesive available from National Starch & Chemical Company, Bridgewater, N.J. The construction adhesive used to attach the wipe and base layers 15, 20 may also be stretchable. The wipe and base layers 15, 20 may also be attached at locations in addition to or other than the perimetric edges 25, 30.

Coupling the wipe layer 15 to the base layer 20 forms the device 10 with an interior space 40.

The base layer 20 may include a liquid impermeable barrier layer (not shown) facing the interior space 40. In one aspect of the present invention, the material of the barrier layer is a polyolefin-type material that can be heat sealed or ultrasonically sealed. In another aspect of the present invention, the material of the barrier layer is a material such as BSTL, a breathable, stretchable, thermal laminate. BSTL and similar materials are described in U.S. Pat. No. 5,695,868 to McCormack et al. and U.S. Pat. No. 5,843,056 to Good et al. In yet another aspect of the present invention, the material of the barrier layer may be SBL as described above, or may be any other suitable material, particularly those described above with reference to the wipe layer 15. In one aspect of the present invention, because the base layer 20 is the layer most likely to contact a user's hand, the barrier layer acts to keep the base layer 20 and thus the user's hand dry. In another aspect of the present invention, the user's hand or one or more fingers may be inserted between the barrier layer and the base layer 20, where the barrier layer again acts to keep the user's hand/finger(s) dry. The barrier layer may also be positioned adjacent a portion of the wipe layer 15 to occlude a portion of the wipe layer 15 from fluid contact, allowing that portion of the wipe layer 15 to remain dry. Separate barrier layers may also be positioned adjacent the base layer 20 and adjacent the wipe layer 15. In another aspect of the present invention, the base layer 20 and the barrier layer may be the same layer.

By virtues of the design and materials chosen for the device 10, the device 10 is preferably designed to be disposable. In this case, disposable means that the device 10 is disposed of, rather than cleaned, after use.

In an alternative aspect of the present invention, the wipe layer 15 and the base layer 20 are two portions of the same piece of material. One of the wipe layer 15 and the base layer 20 is folded over the other of the wipe layer 15 and the base layer 20, and a portion of the perimetric edges 25, 30 are coupled by any means described herein to form the device 10.

In an alternative aspect of the present invention, an additional mitting layer (not shown) of material may be added and attached to a portion of the perimetric edges 25, 30 while leaving at least one end open to form a mitt to be worn by the user. The mitt may be sized for a human hand, or may be sized for one or more human fingers, including taking the form of a finger glove. The mitting layer can be the same size or shape as the device 10, or it may be a different size or shape, such as smaller or larger. In one aspect of the present invention, the mitting layer may be a strap.

The cleaning device 10 further includes a fluid-containing pouch. Three examples of suitable pouches are described herein, although any suitable fluid-containing pouch may be employed.

In one aspect of the present invention shown in FIG. 1, the pouch may be a pouch 50 that includes a top layer 55 having an outer surface 60, and a bottom layer 65 attached to the top layer 55, such as that described in co-pending U.S. patent application Ser. No. 11/125,725, filed on May 9, 2005 and titled "Device with Pull Tab Activation," incorporated herein by reference. The top and bottom layers 55, 65 are attached such that they form and enclose a cavity 70. The top and bottom layers 55, 65 may attached by thermal bonding, although any suitable attachment method may be used. The cavity 70 may be sealed such that it contains a fluid. The pouch 50 may be rectangular, square, circular, oblong, or any other suitable size or shape.

The top layer 55 includes an opening 75 allowing fluid communication between the cavity 70 and the outer surface 60, although the opening 75 is typically initially sealed. The opening 75 may be one or more slits as shown in FIG. 1. In another aspect of the present invention, the opening 75 may be one or more holes, apertures, pin apertures, frangible portions, or may be of any suitable shape or size. The openings 75 may also be non-uniform in size or length. In another aspect of the present invention (not shown), the opening 75 may be positioned between the top and bottom layers 55, 65.

The pouch 50 also includes a seal 80 that is attached to the outer surface 60 of the pouch 50. The seal 80 is affixed to the outer surface 60 such that the seal 80 blocks and thereby seals the opening 75. The seal 80 may be made from 2 mil polyethylene film available from Bemis Company, Inc., although any suitable material may be used. The seal 80 may be affixed to the outer surface 60 using an adhesive such as a pressure-sensitive acrylic adhesive or a frangible sealant polyethylene available from Bemis Company, Inc.

In other aspects of the present invention, the adhesive used to attach the seal 80 to the pouch 50 may include EVA, polyolefins, reactive epoxies, starches, styrenic block copolymers (SBC), natural rubber, polybutylene, acrylics, polyurethanes, epoxies, polyesters, polyamides, silicones, and hot melt adhesives including EVA, SBC, and amorphous poly-alpha-olefin (APAO). Some types of adhesive may require the addition of a tackifier when used with polyethylene film. The adhesive may also be an emulsion-based formula (e.g., PVAc, EVA, rubber such as SBR and neoprene) or solution-based formula (e.g., PVOH, Kymene, and polyethylene oxide). The adhesive may also be a water-based adhesive such as those including either or both of natural and synthetic ingredients, such as polymers, thickeners, fillers, tackifiers, humectants, and wetting enhancers. The adhesive may be a natural adhesive such as starches (e.g., corn, tapioca, and wheat), dextrin, and animal glue.

In one aspect of the present invention, such adhesive is applied only to the portion of the seal 80 that contacts the outer surface 60. Sufficient pulling pressure applied to the seal 80 will overcome the force of the adhesive, causing the seal 80 to release from the outer surface 60, thereby unsealing the opening 75. In manufacture, the seal 80 may be placed on the pouch 50 before the pouch 50 is filled with fluid.

The seal 80 may also include a pull tab 96 extending from the seal 80. The pull tab 96 may be an extension of and formed from the same material as the seal 80, or the pull tab 96 may be formed separately and then affixed to the seal 80. The pull tab 96 and the seal 80 may be together or separately considered to be a pouch extension. Pulling on the pull tab 96 thus pulls on the seal 80, causing the seal 80 to be removed from its position sealing the opening 75. In one aspect of the present invention, the pull tab 96 is folded back across the seal 80 to overlie the seal 80. In this position, pulling the pull tab 96 in a direction generally tangential to the outer surface 60 causes the pull tab 96 to pull on the seal 80. The seal 80 is thus peeled away from the pouch 50 as the seal 80 detaches from the outer surface 60, thereby unsealing the opening 75. In one aspect of the present invention, and to ensure that the pull tab 96 remains in a position overlying the seal 80, the pull tab 96 may be removably attached to the seal 80 using adhesive or any other suitable attachment method. To be clear, the pull tab 96 and the seal 80 may be two regions of a single piece of material.

In still another aspect of the present invention that is not shown, the pouch 50 may include at least one opening 75 in each of the top and bottom layers 55, 60 of the pouch 50. In this aspect, each opening 75 would be sealed by a seal 80, each seal 80 having a pull tab 96. Each opening 75 could be unsealed independently of the other. Each pull tab 96 may be pulled independently, or the pull tabs 96 may be attached to each other to ensure coincident unsealing of the openings 75.

Figure 2:
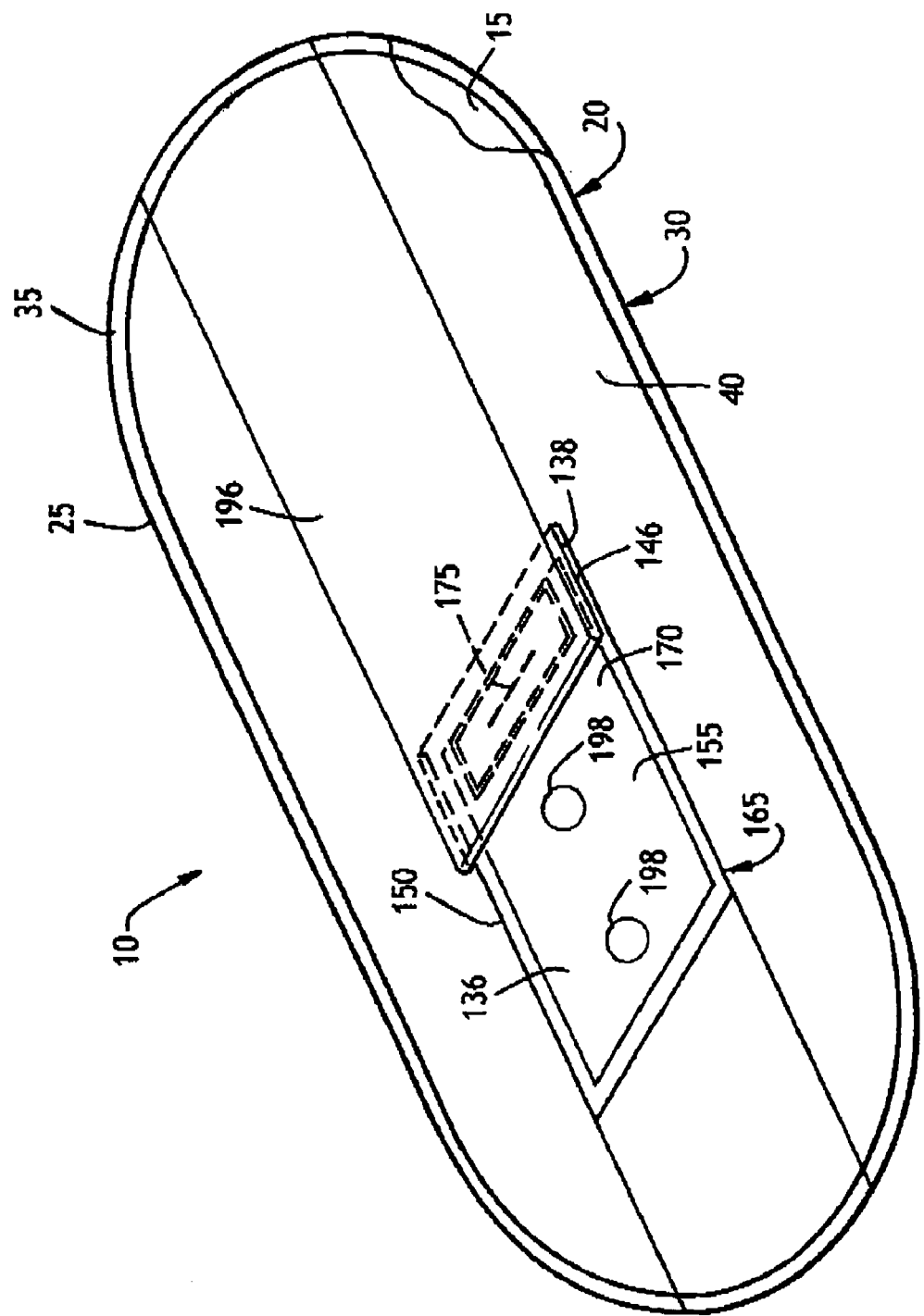
FIG. 2 is a schematic perspective view of another aspect of the invention of FIG. 1.
Figure 3:
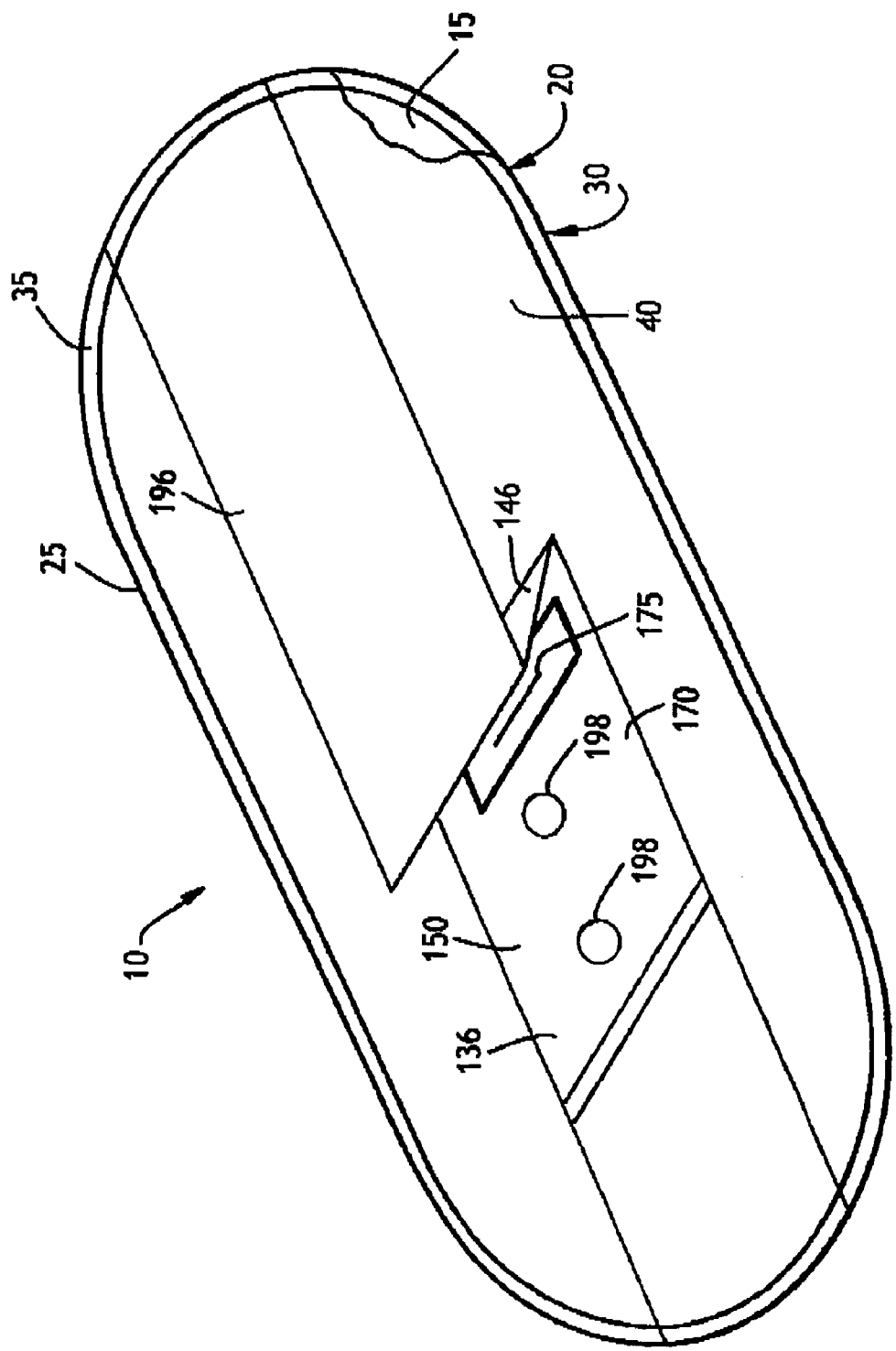
FIG. 3 is a schematic perspective view of the aspect of the invention shown in FIG. 2.

In another aspect of the present invention shown in FIGS. 2 and 3, a pouch 150 contained within a device 10 has a cavity 170 in a first portion 136 of the pouch 150, such as that described in co-pending U.S. patent application Ser. No. 11/217,079, filed Aug. 31, 2005 and titled "Fluid Applicator with a Pull Tab Activated Pouch," incorporated herein by reference. A fluid composition is contained within the cavity 170. The pouch 150 may be formed from opposed layers of material 155, 165 attached together to define the sealed cavity 170, as seen for example in FIG. 2. The opposed layers, a top layer 155 and a bottom layer 165, may attached by thermal bonding, although any suitable attachment method may be used depending on the type of material selected for the top and bottom layers 155, 165.

An exit structure or opening, generally 175, is provided in one of the layers of the pouch 150 through which the fluid composition flows in use of the device 10. Configuration of the opening 175 can vary. For example, the opening 175 may include any pattern of holes, slits, apertures, or other openings defined completely through the respective pouch layer. In alternate embodiments, the opening 175 may be weakened positions in the pouch material or seam structure designed to rupture or burst upon pressure being exerted on the pouch.

FIGS. 2 and 3 illustrate an aspect of a device 10 according to the invention configured as a pad. With this embodiment, the pouch 150 may contain a fluid composition particularly suited for cleaning any manner of surface. To enhance the cleaning effect of the device 10, the wipe layer 15 may include a textured outer face that may be formed from any suitable textured material.

The pouch 150 incorporates a flap 146 that is formed from an extension of the pouch material. For example, the flap 146 may be formed from an extension of the opposed pouch layers 155, 165 that are sealed together in a second portion 138 (FIG. 2) of the pouch 150 that is adjacent to the first portion 136 containing the cavity 170. The flap 146 is folded so as to extend back over the pouch 150 a sufficient distance to cover and releasably seal over the opening 175. A releasable adhesive may be provided between the flap 146 and pouch material to ensure that the flap 146 remains sealed over the opening 175 until the device 10 is ready for use. The flap 146 may be folded a second time in an opposite direction so as to extend back over the first fold of flap 146.

The flap 146 includes a longitudinally extending pull tab 196 that extends outwardly from the pouch 150. The pull tab 196 may be an extension of the flap 146 or it may be a separate piece of material.

When the pull tab 196 is pulled, the flap 146 is caused to unfold and release from the pouch material, and thereby uncover the opening 175 (see FIG. 3). The fluid composition within the cavity 170 is then free to migrate out of the opening 175 in the embodiment wherein the opening 175 includes holes or other openings through the pouch material. In the embodiment wherein the opening 175 includes a frangible or burstable seal, the pouch is activated by the user applying pressure to the pouch causing the opening to open. The fluid composition is then free to migrate into the interior space 40 between the wipe layer 15 and base layer 20, and to migrate through the wipe layer 15. Alternative aspects of the second pouch design are described in co-pending U.S. patent application Ser. No. 11/217,079, filed Aug. 31, 2005 and titled "Fluid Applicator with a Pull Tab Activated Pouch," incorporated herein by reference.

Figure 4:
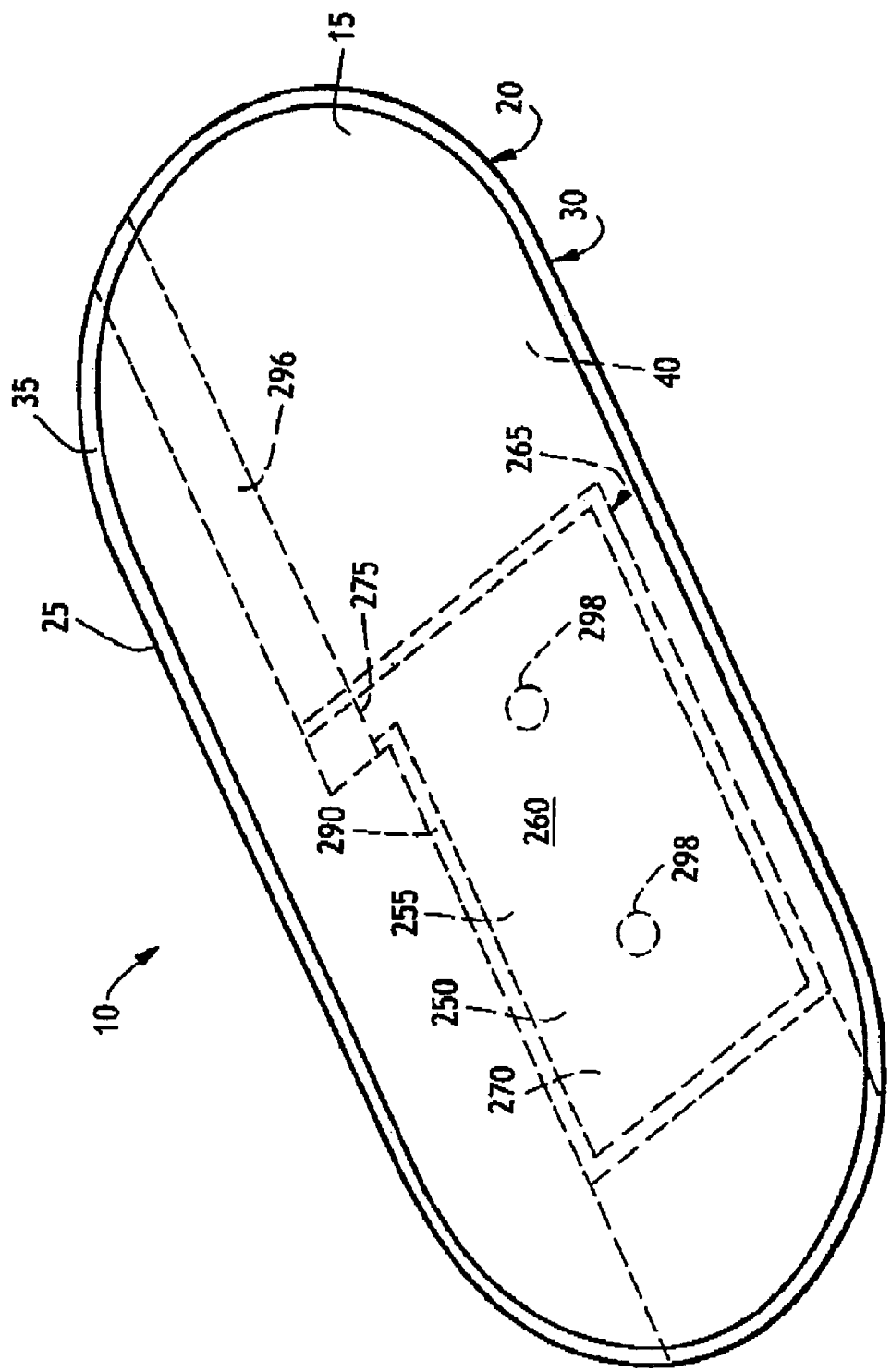
FIG. 4 is a schematic perspective view of another aspect of the invention of FIG. 1.
Figure 5:
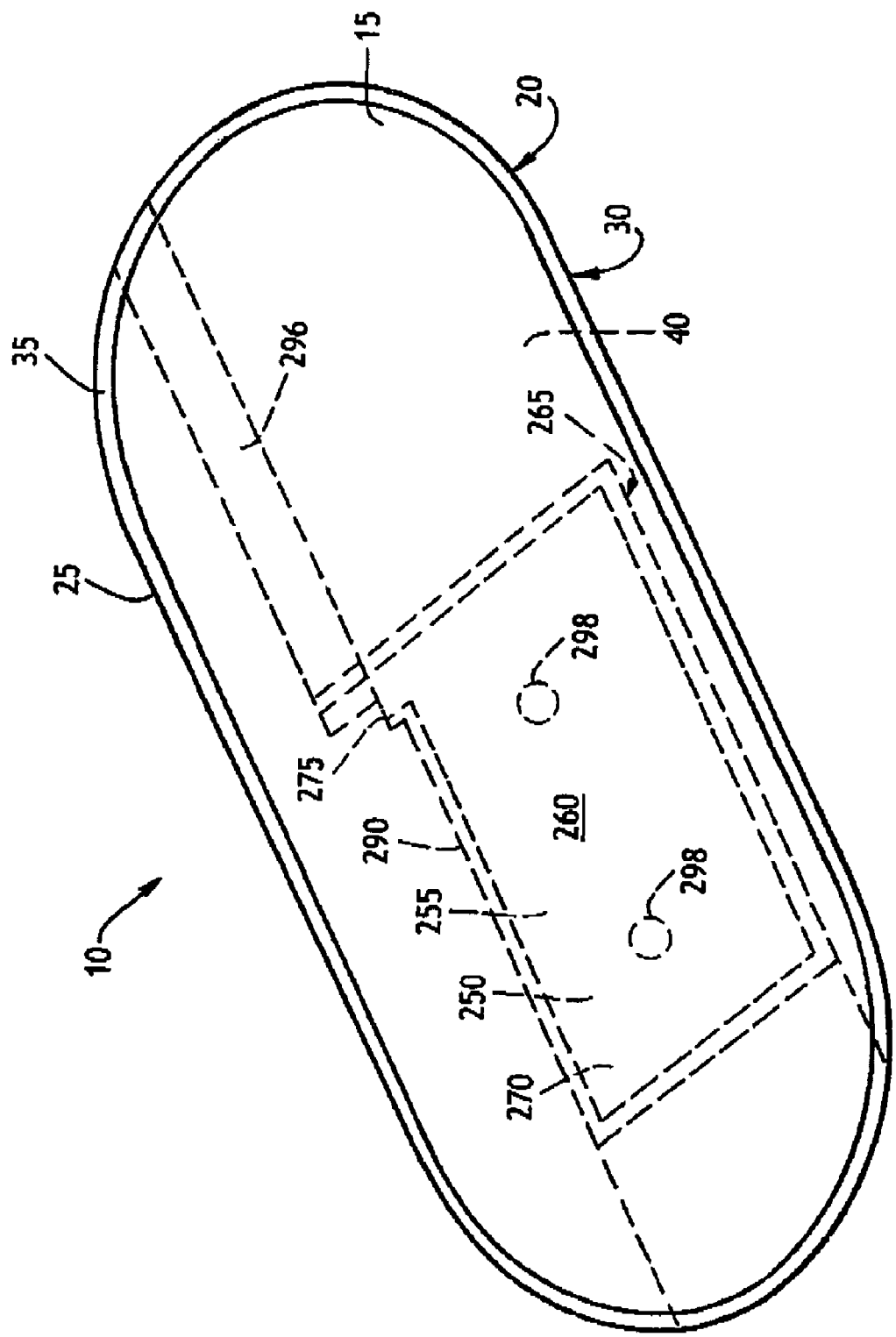
FIG. 5 is a schematic perspective view of the aspect of the invention shown in FIG. 4.

In another aspect of the present invention shown in FIGS. 4 and 5, the pouch may be a pouch 250 that includes a top layer 255 having an outer surface 260, and a bottom layer 265 attached to the top layer 255. The top and bottom layers 255, 265 are attached such that they form and enclose a cavity 270 and such that they form a pouch edge 290. The top and bottom layers 255, 265 may attached by thermal bonding, although any suitable attachment method may be used. The cavity 270 may be sealed such that it contains a fluid. The pouch 250 may be rectangular, square, circular, oblong, or any other suitable size or shape.

In one aspect of the present invention, the pouch includes an opening 275 in the pouch edge 290 through which the contents of the pouch 250 may be expelled, although technically the opening 275 does not exist until the pouch 250 is activated. The opening 275 may be configured and sized such that the opening 275 acts as a metering port to limit the rate at which the pouch contents may be expelled. The opening 275 may be made a metering port by any suitable method. In another aspect of the present invention (not shown), the pouch 250 may include a metering port spaced apart from the opening 275. A metering port allows the contents of the pouch 250 to be dispensed on demand as a user applies pressure to the device 10, instead of releasing the contents of the pouch 250 all at once.

The pouch 250 further includes an activation or pull tab 296 attached to the pouch 250 and closing the opening 275. In one aspect of the present invention, the pull tab 296 is formed with the pouch 250 and then partially separated from the pouch 250 by cutting, slitting, or otherwise creating a separation between the pull tab 296 and the pouch 250. The attachment point between the pull tab 296 and the pouch 250 that closes the opening 275 may be tearable or frangible such that the pull tab 296 is further separated from the pouch 250 when the pull tab 296 is pulled. For example, the separation between the pull tab 296 and the pouch 250 may terminate in a stress concentration notch to facilitate tearing the pull tab 296 either partially or completely from the pouch 250.

The pull tab 296 extending from the pouch 250 may be an extension of and formed from the same material as the pouch 250, or the pull tab 296 may be formed separately and then affixed to the pouch 250. Pulling on the pull tab 296 thus causes the pull tab 296 to be removed from its position sealing the opening 275 (see FIG. 5). In one aspect of the present invention, the pull tab 296 is folded back across the pouch 250 to overlie the pouch 250. In this position, pulling the pull tab 296 in a direction generally tangential to the outer surface 260 causes the pull tab 296 to separate from the pouch 250, thereby unsealing the opening 275. In one aspect of the present invention, and to ensure that the pull tab 296 remains in a position overlying the pouch 250, the pull tab 296 may be removably attached to the outer surface 260 of the pouch 250 using adhesive or any other suitable attachment method.

For any of the pouch configurations described herein, the pouch 50, 150, 250 is positioned within the interior space 40 of the device 10. The pouch cavity 70, 170, 270 may be sealed prior to being filled or partially filled with one or more fluids. The pouch 50, 150, 250 may be any size that fits within the interior space 40, with the size selected based on the fluid to be housed and the intended use of the device 10.

The pouch 50, 150, 250 can be sized to provide a level of over saturation that permits the fluid to soak through the wipe layer 15, permitting it to be absorbed by the intended surface. An example of this would be a stain removal cloth for carpet cleaning where it is desired to soak the stain.

The pouch 50, 150, 250 is made from a flexible, heat sealable material such as 2 mil polyethylene film available from Bemis Company, Inc. In other aspects of the present invention, the pouch 50, 150, 250 may be made from polyethylene, polypropylene, or other suitable thermoplastics, or from a high liquid barrier material such as a metal foil or a metalized film. The material from which the pouch 50, 150, 250 is made should have no negative impact on or reaction with the fluid to be contained in the pouch 50, 150, 250. The materials used in the construction of the pouch 50, 150, 250 and the fill level of the fluid within the pouch 50, 150, 250 create a structure that is durable and flexible, and one that is not easily burst open during normal handling. In one aspect of the present invention, the pouch 50, 150, 250 is bonded to one of the wipe layer 15, base layer 20, or barrier layer.

In one aspect of the present invention, the pouch 50, 150, 250 may also include one or more bonding points 98, 198, 298 at which the top layer 55, 155, 255 is affixed to the bottom layer 65, 165, 265. The bonding points 98, 198, 298 may be formed by any method described above for affixing the top layer 55, 155, 255 to the bottom layer 65, 165, 265 to form the pouch 50, 150, 250. The bonding points 98, 198, 298 act to inhibit the top layer 55, 155, 255 from moving relative to the bottom layer 65, 165, 265 when force is applied to the pull tab 96, 196, 296. In one aspect of the present invention, the bonding points 98, 198, 298 may be positioned within the cavity 70, 170, 270 and spaced apart from the edges of the pouch 50, 150, 250. Although described as points, in other aspects of the present invention the bonding points 98, 198, 298 may be lines, geometric shapes, or any other suitable shapes or sizes.

In another aspect of the present invention, the pouch 50, 150, 250 may include a baffle (not shown) disposed inside the pouch 50, 150, 250 to control the rate of fluid release from the pouch 50, 150, 250. The baffle may be manufactured from any suitable spongy, fibrous, or porous material.

In one aspect of the present invention, the pull tab 96, 196, 296 may extend to the perimetric edges 25, 30 of the wipe and base layers 15, 20 (see FIGS. 1 and 3). The pull tab 96, 196, 296 may be incorporated into the seam 35 or otherwise attached to one or more of the wipe layer 15, base layer 20, and barrier layer. This arrangement allows the pull tab 96, 196, 296 to be manipulated by a user without actually touching the pull tab 96, 196, 296 when the pouch 50, 150, 250 is positioned within the interior space 40. Pulling on the perimetric edges 25, 30 pulls on the pull tab 96, 196, 296 as well. The pull tab 96, 196, 296 may thereby remain within the interior space 40. The pouch 50, 150, 250 may also be incorporated into the seam 35 or otherwise attached to one or two of the wipe layer 15, base layer 20, and barrier layer.

In conjunction with any of the pouch configurations described herein, and in another aspect of the present invention that is not shown, the device 10 may include a line of stitching, glue, or other suitable means to define a pocket within the interior space 40 to hold a pouch 50, 150, 250 in place.

In another aspect of the invention that is not shown, a distribution layer may be interposed between the pouch and the Wipe layer 15 to ensure fluid is distributed across the wipe layer 15. The distribution layer may be, for example, a surge material that wicks fluid to a substantial portion of the wipe layer 15.

In yet another aspect of the present invention, distribution of fluid into the wipe or base layers 15, 20 may be controlled by using materials with different wicking and other properties that will absorb and distribute the fluid in different patterns, rates, and manners.

The fluid contained in the cavity of the pouch may be any fluid suitable for the intended use of the device 10, including cleansing fluids for human/animal use and cleaning fluids for cleaning surfaces. The fluid may be any paste, gel, powder, oil, liquid, or any other appropriate medium. Example cleansing fluids include surfactants such as water-soluble polymers, polysorbates, glycerins, glycol-based surfactants, and/or silicone-based surfactants. The fluid may include other materials, such as water, salts, vinegars, humectants, scouring powders, thickening agents, and fragrances. A cleansing fluid may also include a moisturizer that helps to maintain a normal skin hydration level. A cleansing fluid may also include preservatives and other ingredients that do not disrupt the skin (e.g., sorbic acid, citric acid, methyl paraben, and natural preservatives such as grapefruit extract). The fluid may include other materials that may be applied to an area of the body. Example materials include lubricants, deodorants, and other inactive or active ingredients (e.g., spermicidal agent or medication). In one aspect of the present invention, the fluid is a cleansing fluid that is primarily a water-based solution (greater than or equal to 90 percent water content) with a surfactant, preservatives, pH neutralizers, and a thickening agent. The fluid may be a lotion or an emulsion. Non-limiting examples include sunless tanning lotion, leather conditioning lotion, and depilatory lotion.

The fluid may be a cleaning solution such as FOUR PAWS Super Strength Stain and Odor Remover, which includes water, natural enzymes, and mild detergent (from Four Paws Products, Ltd., Hauppauge, N.Y.), or NATURE'S MIRACLE Stain & Odor Remover, which includes water, natural enzymes, isopropyl alcohol, and natural citrus scent (from Pets 'N People, Inc., Rolling Hills Estates, Calif.), or RESOLVE Carpet Spot & Stain Carpet Cleaner (from Reckitt Benckiser, Wayne, N.J.). The fluid may be a pet shampoo. The fluid may be a stain cleaner and stain guard such as SCOTCH-GARD Oxy Carpet Cleaner with Stain Protector that includes water, 2-butoxyethanol, hydrogen peroxide, and surfactants (from 3M Corporation, St. Paul, Minn.). In the case of using the cleaning device 10 to clean a fabric surface, the fluid may include a pet repellant such as SIMPLE SOLUTION Indoor/Outdoor Repellent for Dogs and Cats, which has as an active ingredient methyl nonyl ketone (from The Bramton Company, Dallas, Tex.).

The fluid may be an antimicrobial. Examples of suitable antimicrobials include quaternary ammonium compounds such as 3-trimethoxysilylpropyldimethyloctadecyl ammonium chloride (AEGIS); poly cationic chemicals such as biguanides (poly (hexamethylene) biguanide hydrochloride (PHMB) Arch Chemical), 2,4,4'-Trichloro-2'-hydroxyl-dipenylether (Tinosan, Ciba); diphenyl ether (bis-phenyl) derivatives known as either 2,4,4'-trichloro-2' hydroxy dipenyl ether or 5-chloro-2-(2,4-dichlorophenoxyl) phenol; triclosan; silver; and copper. The fluid may be an allergen sequestrant that may be a charged or mixed charged particle or nanoparticle. Most allergy proteins are glycoproteins (proteins that contain covalently-bound oligosaccharides), so a negative charge may be better then predominance of positive charges on the particles, although mixed charges may be preferred. Clays or modified clays work in this respect. Examples of suitable allergen sequestrants include plant lectins with an affinity for N-acetylgalactosamine such as jacalin, peanut, and soybean, where the lectins both bind allergens and are bound to the web, thus removing allergens from a surface. The fluid may also include a fragrance. The fluid may also include a pheromone to either attract or repel an animal. The fluid may also be shoe polish, a carpet cleaning solution, a stain removal fluid, kitchen floor and counter top cleaners, etc.

In use, a user grasps each end and pulls the ends away from each other, causing the pull tab 96, 196, 296 to unseal the opening 75, 175, 275. If desired, the device 10 may be held in a vertical or other suitable position such that only a limited amount of the contents of the pouch 50, 150, 250 is dispensed from the pouch 50, 150, 250 at a time. With the device 10 held in such a position, there is little loss of contents until the device 10 is squeezed, tilted, or otherwise manipulated. By using the device in this manner, the device may 10 may be used for an extended application because the contents are rationed across the intended use.

Example 1

In an example of an aspect of the present invention, a cleaning device 10 was manufactured. The wipe layer 15 was formed from a dry embossed 110 grams per square meter (gsm) coform laminate available from Kimberly-Clark Corporation. The base layer 20 was formed from a dry embossed 110 gsm coform laminate available from Kimberly-Clark Corporation. The wipe layer 15 was coupled to the base layer 20 by ultrasonic bonding. The pouch 50 was formed from 2 mil polyethylene film available from Bemis Company, Inc. and was positioned within the interior space 40. The pull tab 96 was formed from 2 mil polyethylene film available from Bemis Company, Inc. The fluid injected into the cavity 70 just prior to completely sealing the pouch 50 was distilled water. A frangible bond was formed between the outer face 60 and the pull tab 96. The completed device 10 was subjected to various manual manipulations consistent with shipping and handling without rupturing the pouch 50. Finally, the pull tab 96 was pulled, thereby unsealing the pouch 50 and resulting in the wipe layer 15 becoming wet from the fluid contents of the pouch 50.

Example 2

In an example of an aspect of the present invention, a cleaning device 10 was manufactured. A foil pouch 250 was partially formed in the configuration described above using a heat sealer. The pouch 250 was filled with 5.5 grams of Turtle Wax Max Black Tire Dressing using a 5 ml syringe. The final edge of the pouch 250 was sealed using the heat sealer. The edge 290 of the pouch 250 was trimmed to form a pull tab 296 for easy opening of the pouch 256. The pouch 250 was glued to the inside surface of a 3.7 osy point unbonded polypropylene nonwoven using a hot melt adhesive glue gun. This assembly was placed on an anvil bond pattern, followed by a layer of a film/nonwoven laminate, and finally a layer of necked bonded laminate. The layers were bonded together around the perimeter along three sides using a Branson ultrasonic plunge bonder resulting in a multi-finger device 10. Care was given to ensure that neither the pull tab 296 nor the pouch 250 was damaged by the bonding.

The pull tab 296 was pulled, which opened the opening 275 in the pouch 250. The device 10 was placed on the three middle fingers of a user's hand. Squeezing the device 10 and thus the pouch 250 dispensed the contents of the pouch 250 at a metered rate.

Embodiments of the invention have been described with reference to various specific and illustrative aspects and techniques. However, it should be understood that many variations and modifications may be made while remaining within the spirit and scope.

Accordingly, this is intended to embrace all such alternatives, modifications and variations that fall within the spirit and scope of the appended claims.

We claim:

1. A device comprising:
 a stretchable base layer;
 an elastically stretchable wipe layer attached to the base layer at a seam and defining an interior space between the wipe and base layers, the interior space having an internal surface; and
 a pouch positioned within the interior space and attached to one of the seam and the internal surface, the pouch having
 a top layer,
 a bottom layer attached to the top layer to form a cavity therebetween,
 an opening in one of the top and bottom layers, and
 a pull tab coupled to the pouch and to one of the seam and the internal surface.

2. The device of claim 1, wherein the pouch is configured such that the opening is uncovered when the pull tab is pulled.

3. The device of claim 1, wherein the pouch is configured such that a tear is created at a specified location when the tab is pulled.

4. The device of claim 1, further comprising a barrier layer interposed between the pouch and the base layer.

5. The device of claim 4, wherein the device is a finger glove.

6. The device of claim 1, wherein the device is a pad.

7. The device of claim 1, wherein the device is a mitt.

8. The device of claim 1, wherein the pouch is attached at the seam.

9. The device of claim 1, wherein the pull tab is attached at the seam.

10. The device of claim 1, wherein the base layer is elastically stretchable.

11. The device of claim 1, wherein the opening is a slit.

12. The device of claim 1, wherein the opening includes a frangible portion.

13. The device of claim 1, wherein the opening is sealed by a portion of the pouch.

14. The device of claim 1, wherein the pull tab is attached to the pouch using adhesive.

15. The device of claim 1, wherein the pull tab is formed from one of the top and bottom layers.

16. The device of claim 1, further comprising a bonding point affixing the top layer to the bottom layer.

17. The device of claim 1, wherein the wipe layer and the base layer are two portions of the same piece of material.

18. The device of claim 1, further comprising a second pouch positioned within the interior space.

19. A device comprising:
 an elastically stretchable base layer;
 a stretchable wipe layer attached to the base layer to form an internal space therebetween;
 a means for containing a fluid positioned within the internal space; and
 a means for unsealing the fluid-containing means, wherein the unsealing means is activated by stretching both the wipe and base layers.

20. A method for using a device, the method comprising:
 producing a device including a base layer and a wipe layer attached to the base layer at a seam and defining an interior space between the wipe and base layers, the interior space having an internal surface, wherein one of the wipe and base layers is stretchable; and activating the device by stretching the device by applying a tensile force to the device in a longitudinal direction with respect to the wipe and base layers.

21. The method of claim 20, further comprising a pouch positioned within the interior space and attached to one of the seam and the internal surface, the pouch having a pull tab coupled to the pouch and to one of the seam and the internal surface.

22. The method of claim 21, wherein stretching the device opens the pouch.

23. A method for using a device, the method comprising:

producing a device including a base layer;

a wipe layer attached to the base layer at a seam and defining an interior space between the wipe and base layers, the interior space having an internal surface; and a pouch positioned within the interior space and attached to one of the seam and the internal surface, the pouch having a top layer, a bottom layer attached to the top layer to form a cavity therebetween, an opening in one of the top and bottom layers, and a pull tab coupled to the pouch and to one of the seam and the internal surface; and activating the device by stretching the device to open the opening.

* * * * *